United States Patent [19]
Baer et al.

[11] Patent Number: 5,322,607
[45] Date of Patent: Jun. 21, 1994

[54] ELECTRICAL POTENTIAL CONFIGURATION FOR AN ELECTROPHORESIS SYSTEM

[75] Inventors: Richard L. Baer, Los Altos, Calif.; Jurgen A. Lux, Niederkirchen, Fed. Rep. of Germany; James E. Young, La Honda, Calif.

[73] Assignee: Hewlett-Packard Company, Palo Alto, Calif.

[21] Appl. No.: 913,123

[22] Filed: Jul. 14, 1992

[51] Int. Cl.⁵ .............................. C25B 9/00
[52] U.S. Cl. ............................. 204/299 R
[58] Field of Search ................... 204/299 R

[56] References Cited

U.S. PATENT DOCUMENTS

| | | | |
|---|---|---|---|
| 4,705,616 | 11/1987 | Andresen et al. | 204/299 R |
| 4,842,701 | 6/1989 | Smith et al. | 204/180.1 |
| 4,898,658 | 2/1990 | Karger et al. | 204/299 R |
| 4,936,974 | 6/1990 | Rose et al. | 204/299 R |
| 4,940,883 | 7/1990 | Karger et al. | 219/200 |
| 5,021,646 | 6/1991 | Weinberger et al. | 250/227.11 |
| 5,180,475 | 1/1993 | Young et al. | 204/180.1 |

FOREIGN PATENT DOCUMENTS 55-40048 10/1981 Japan.
1-312907 7/1991 Japan.

Primary Examiner—John Niebling
Assistant Examiner—C. Delacroix-Muirheid

[57] ABSTRACT

An electrophoresis system having separate internal and external voltage gradients that are vectorially coupled to determine zeta potential along the interior surface of a capillary column. The voltage gradient along the exterior of the capillary column is established such that the electrical potential at an on-column detection area is substantially equal to the electrical potential of a detector used to sense electrophoretic migration past the detection area. Typically, the capillary column is grounded at the point of detection, with the exterior voltage gradient being positive-going in one direction from the point of detection and being negative-going in the opposite direction.

19 Claims, 4 Drawing Sheets

ELECTRICAL POTENTIAL CONFIGURATION FOR AN ELECTROPHORESIS SYSTEM

DESCRIPTION

1. Technical Field

The present invention relates generally to electrophoretic systems and more particularly to a system having external control of electroosmotic flow along a capillary column.

2. Background Art

Applications for electrophoresis, an analytical technique for separating and identifying constituents in a sample, include the determination of a sample's purity, the determination of molecular weights for proteins and nucleic acids, the mapping of nucleic acid primary structures, i.e. DNA and RNA sequence analyses, and the definition of phenotypic variance of a protein at the molecular level. Electrophoretic techniques rely on the fact that each molecular species has a unique combination of mass, size, shape, charge, density and sub-unit structure, all of which result in mobility differences responsive to an electric field. Various electrophoretic techniques use one or more of these properties to cause varying degrees of molecular separation via the migration of molecular species under an electric field.

Capillary electrophoresis is a technique using a capillary tube which is filled with a conductive fluid, as for example a buffer solution. A small amount of sample is introduced at one end of the capillary tube, whereafter a high potential difference is applied across the ends of the tube. Electroosmotic flow and differences in electrophoretic mobilities combine to provide a spatial separation of constituents of the sample solution at the outlet end of the capillary tube.

Electroosmotic flow is the movement of a liquid relative to a stationary charge surface as a result of electric fields applied to the liquid. U.S. Pat. No. 4,936,974 to Rose et al. explains electroosmotic flow as a result of charge accumulation at the interior capillary surface due to preferential adsorption of anions from the buffer solution that fills the bore of the capillary tube. The negative charge of the anions attracts a thin layer of mobile positively charged buffer ions which then accumulate adjacent to the inner surface. The charge accumulation at the interior wall provides a radially extending electric field. The potential across this radially extending electric field is referred to as the "zeta potential." The longitudinally extending electric field that is applied across the capillary tube attracts the positive ions which are hydrated by water toward a grounded outlet end of the capillary tube, viscously dragging other hydrated molecules. This dragging of molecules applies to neutral and negatively charged molecules, as well as positively charged molecules. The result is a bulk flow of the sample in the buffer solution toward the grounded outlet end of the capillary tube. Consequently, electroosmotic flow provides a means for moving neutral and negatively charged constituents of a sample toward a ground electrode.

Electrophoretic migration is the movement of charged constituents in response to an electric field applied along the longitudinal axis of the capillary tube. A positively charged molecule will be accelerated through the electroosmotic flow toward the ground electrode. Negatively charged molecules may be repelled by the ground electrode, but the force of the electroosmotic flow overcomes the repulsion and advances the negatively charged molecules.

As a result of the combination of electroosmotic flow and electrophoretic migration for an analysis in which a positive electrode is applied to the inlet end of the capillary tube and a ground electrical is applied to the outlet end, a spatial separation will occur with positively charged constituents exiting first, followed by neutral constituents and then negatively charged constituents. Each constituent of a sample may be identified by detecting the time required for the constituent to travel through the capillary tube. The quantity of the constituent within the sample is determined by the height and/or area of a signal trace on an electropherogram during a period of detection of that constituent.

An "on-column detector" detects migration of sample constituents past a detection area of the capillary tube between the inlet end and the outlet end. Ultraviolet and fluorescence on-column detectors are common. Alternatively, detection can take place after release of the sample from the outlet end, i.e., "off-column detection." For example, U.S. Pat. Nos. 4,705,616 to Andresen et al. and 4,842,701 to Smith et al. describe electrospraying the separated solution from the outlet end for off-column detection by mass spectrometry.

Obtaining an accurate analysis requires that each sample constituent be moved to the detection area. Often, the sample is introduced into the inlet end of the capillary tube by insertion of the inlet end into a sample vial, whereafter the inlet end is inserted into a first buffer vial electrically connected to a high voltage electrode. The outlet end of the capillary tube is inserted into a buffer reservoir vial connected to the ground electrode. Upon initiating the separation procedure, a negatively charged molecule may be drawn into the first buffer vial before electroosmotic flow can take full effect. Thus, these molecules will not be detected, rendering the analysis less accurate. Another problem in obtaining an accurate analysis involves the resolution of constituent detections. If a sample contains a number of constituents having similar electrophoretic mobilities, an analysis may be susceptible to errors in identifying and in quantifying the constituents. Yet another problem involves external factors, such as atmospheric conditions, that may have an effect on the electrophoretic separation.

U.S. patent application Ser. No. 07/754,797, to Young et al. which is assigned to the assignee of the present application and is incorporated herein by reference, describes a system and method for controlling electroosmotic flow and reducing undesired effects of external influences, thereby improving the analytic procedure. The rate of electroosmotic flow is directly proportional to the permittivity of the solution, the longitudinal axial electrical field and the zeta potential and is inversely proportional to the viscosity of the solution. Young et al. teach that the zeta potential can be controlled by providing a coating of electrically conductive material on the outside wall of the capillary tube. The conductive coating reduces the likelihood that an undesired voltage gradient will be created along the outside wall. A controlled field along the outside wall prevents external forces from affecting the internal ionic charge at the interior wall of the capillary tube. The electrically conductive coating may be allowed to float, but preferably is grounded to reduce the likelihood of electrostatic charges on the outside wall of the capillary tube.

Okubo in Japanese Application No. Sho 55-40048 describes use of a transparent conductive coating that is uniformly charged by a power source. The uniform charge on the transparent coating is selectively turned off to compare the movement of sample constituents before and after the switching of the charge. The comparison provides data for determining what is referred to as the actual electrophoresis speed. The particle movement is determined by use of directing laser light through an electrophoresis tube.

While a number of on-column detectors are known, ultraviolet detectors provide many advantages. However, a UV detector is preferably positioned as close to a capillary tube as possible, thereby preventing ambient light from entering the capillary tube at the detection area. The entrance of ambient light would adversely affect the analytical technique. The problem with the close coupling of a UV detector to a capillary tube having a charge at its exterior is that the exterior charge may cause a coronal discharge to the UV detector, which is typically grounded.

It is an object of the present invention to provide an electrophoresis system having on-column detection and control of electroosmotic flow without rendering the system susceptible to electrical discharge from a capillary tube to an on-column detector.

SUMMARY OF THE INVENTION

The above object has been met by an electrophoresis system having a capillary column that includes a resistive coating, with a positive-going portion of the coating on a first side of an on-column detection area and a negative-going portion on an opposite side. That is, the resistive coating is at ground potential at the on-column detection area, thereby eliminating electrical discharge from the resistive coating to a detector as a source of disruption of an analysis.

High voltage power supplies are utilized to provide a first longitudinal voltage gradient along an axial bore of the capillary column and to create a second longitudinal voltage gradient along the resistive coating. Preferably, the second voltage gradient is created by applying a positive high voltage at a first end of the resistive coating and applying a negative high voltage at a second end, with the high voltages being selected so that the gradient is uniform and so that a ground potential is established at the point of detection. For example, a first high voltage power supply can be attached with a grounded electrode at the on-column detection area and a positive electrode at the first end, while a second high voltage power supply has a grounded electrode at the on-column detection area and a negative electrode attached at the second end of the resistive coating.

The resistive coating must be made of a material having high resistivity. The material may be a dielectric having a relatively low concentration of conductive material. For example, a layer of cross-linked polyimide having a concentration of less than ten percent carbon black may be used. The voltage gradient along the resistive coating is selected to achieve a desired zeta potential at the interior of the capillary column.

An advantage of the present invention is that a grounded on-column detector may be brought close to or even in contact with an electroosmotic flow-affecting exterior of a capillary tube without risk of causing an electrical discharge, despite the application of a high voltage to the tube exterior. An electrical discharge from a high voltage tube exterior to a grounded detector would significantly disturb electrophoretic analysis. By setting the electrical potential at the point of detection to a voltage substantially equal to the potential of the on-column detector, electrical discharge is inhibited, thereby providing a desirable baseline for UV detection. While the invention has been described above as being grounded at the point of detection, what is important is that the potential at this point and the potential of the detector must be substantially equal.

An alternative to the present invention would be to provide additional layers of insulating materials over the resistive coating, so as to insulate the resistive coating from the detector. However, this would lead to a significant loss in the sensitivity of UV detection. The combination of a resistive coating and a thin insulating layer may however provide advantages, as for example to guard against electrical discharge to components other than the detector.

BEST MODE FOR CARRYING OUT THE INVENTION

Figure 1:
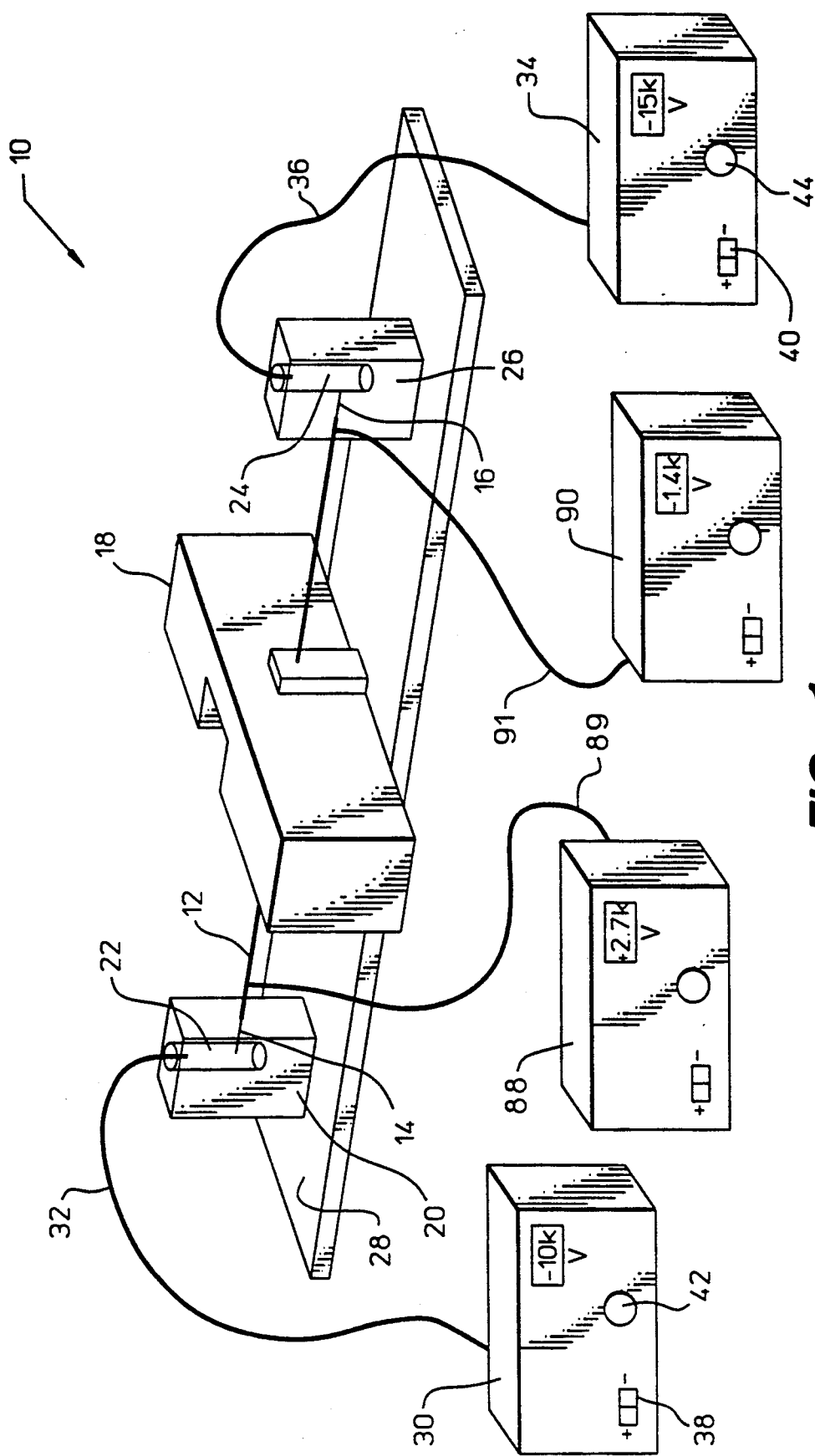
FIG. 1 is a schematic view of an electrophoresis system having on-column detection and having external control structure for affecting the rate of electroosmotic flow through a capillary tube of the system.

With reference to FIG. 1, an electrophoresis system 10 is shown as including a capillary tube 12 having an inlet end 14 and an outlet end 16. The capillary tube is of the type known in the art. A fused silica tube having a coating of polyimide may be used. Such a capillary tube is flexible but has a material memory that urges the tube to return into a generally straight condition after flexing. The capillary tube has an inside diameter of 50 microns and an outside diameter that is typically in the range of 140 microns to 360 microns, but these dimensions are not critical.

An on-column detector 18 is located along the length of the capillary tube 12. The polyimide coating is removed from the capillary tube at the optical coupling of the tube to the detector. U.S. Pat. No. 4,940,883 to Karger et al. describes a device for removing a polymer from a portion of a capillary tube to provide a detection window for on-column detection. In capillary zone electrophoresis, ultraviolet absorbance detectors are commonly used, but other detectors are known. For example, detection may also occur using a chemi-luminescence, refractive index, or conductivity detector. The optical coupling of the detector to the capillary tube permits detection of movement within the capillary tube.

The inlet end 14 of the capillary tube 12 is inserted into a container 20 having a supply vial 22. At the opposite side of the detector 18 is a buffer reservoir vial 24 that is in fluid communication with the outlet end 16 of the capillary tube. The buffer reservoir vial is housed within a container 26. The two containers 20 and 26 and the detector 18 are shown as resting on a table 28.

A first high voltage power supply 30 is electrically connected to the supply vial 22 via a power line 32 that represents an anode electrode. The first power supply 30 provides a high voltage, shown in FIG. 1 as −10k volts, at the supply vial 22. However, this high voltage is not the potential difference across the capillary tube 12. The potential difference is determined by the voltage at the buffer reservoir vial 24. This voltage is provided by a second high voltage power supply 34 in electrical communication with the buffer reservoir vial 24 via a power line 36 that represents the cathode electrode. The second power supply 34 is illustrated as being set to provide a second high voltage of −15k volts. Thus, the potential difference across the capillary tube 12 is 5k volts. A standard potential gradient in capillary zone electrophoresis is 200v/cm. To achieve this standard, the length of the capillary tube 12 would then be 25 cm.

Each of the high voltage power supplies 30 and 34 is a bipolar device having a polarity-select switch 38 and 40 to adjust the polarity of the associated electrode 32 and 36. Voltage-adjustment dials 42 and 44 allow a user to accurately set the outputs of the power supplies. The rate of electroosmotic flow through the capillary tube 12 may be varied while maintaining the same potential gradient by providing corresponding adjustments of the first and second power supplies 30 and 34. That is, a change in the voltage offset relative to ground changes the electroosmotic flow rate and, therefore, the time required to complete an analysis of a particular sample. For example, using the electrophoresis system of FIG. 1 in which the capillary tube has an inside diameter of 50 microns and an outside diameter of 140 microns, with the respective voltages set at −15k volts and −10k volts, a particular analysis requires a migration time of eighty minutes. By varying the voltage offset upwardly relative to ground, the flow rate is increased, so that the same analysis can take place in a much shorter time, e.g., seventeen minutes where each power supply is increased by 15k volts to ground and +5k volts. A corresponding negative adjustment to the two power supplies, i.e. a decrease in the voltage offset relative to ground, decreases the electroosmotic flow rate.

Figure 2:
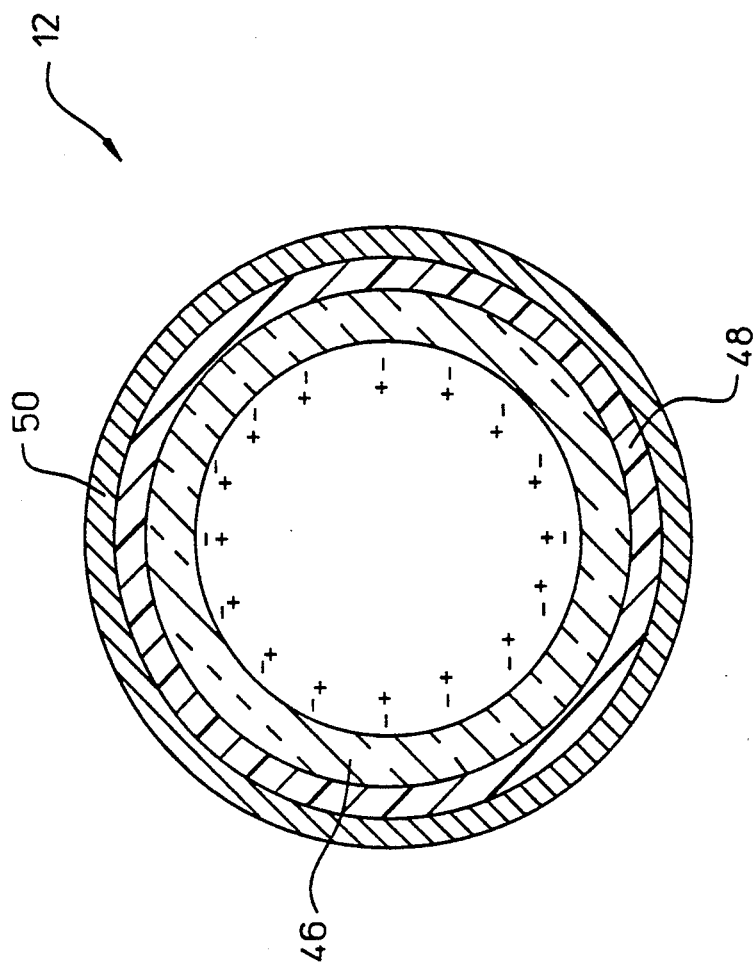
FIG. 2 is a front sectional view of the capillary tube of FIG. 1.

In addition to an adjustment of the voltage offset relative to ground, electroosmotic flow rate can be affected by providing a resistive coating to the capillary tube 12. Referring now to FIG. 2, the capillary tube 12 is shown as including a fused silica capillary layer 46, and a polyimide layer 48. These two layers 46 and 48 are standard in the art. The capillary tube 12 also includes a resistive coating 50. By "resistive coating" what is meant is a conductive coating or layer having a high resistance that may be utilized to establish an electrical field along the capillary tube. Optionally, the layers 48 and 50 may be combined into a single layer to provide a conductive polymer. For example, a cross-linked polyimide containing 7.5 percent carbon black may be used. The thickness of such a coating would determine the bulk resistivity and the sheet resistance of the coating. One practical option would be to provide a coating of a thickness to achieve a bulk resistivity of approximately 2K ohms-cm and a sheet resistance of approximately 2M ohms per square.

The two high voltage power supplies 30 and 34 provide an electrical field along the longitudinal axis of the capillary tube 12. As illustrated by the symbols "+" and "−" in FIG. 2, a radially extending electrical field is also created. A charge accumulation at the interior capillary surface results from preferential adsorption of anions from the buffer solution that fills the migration path of the capillary tube. The negative charge of the anions attracts a thin layer of mobile positively charged buffer ions. The electrical potential is referred to as "zeta potential." Electroosmotic flow is a direct result of this double layer of ions formed on the interior capillary surface. Consequently, any charge at the exterior of the capillary tube has a potential of affecting ion collection and electroosmotic flow.

Returning to FIG. 1, in addition to the first and second high voltage power supplies 30 and 34, there are third and fourth high voltage power supplies 88 and 90. The third high voltage power supply 88 has an electrode lead 89 attached to the resistive coating of the capillary tube 12 at the inlet end 14 of the tube. In like manner, the fourth high voltage power supply 90 has an electrode lead 91 attached to the outlet end 16. The removal of resistive material at the inlet and outlet ends of the capillary tube isolates the high voltage power supplies 88 and 90 from high voltage power supplies 30 and 34.

The first and second high voltage power supplies 30 and 34 create a longitudinal voltage gradient along the axial bore of the capillary tube 12, as described more fully above. The third and fourth high voltage power supplies 88 and 90 create a longitudinal voltage gradient along the resistive coating on the capillary tube. The voltage gradient along the resistive coating provides a varying zeta potential at the interior of the capillary tube. This technique vectorially couples the externally applied potential with the potential along the axial bore of the capillary tube. The electrical potential at the exterior of the capillary tube determines the polarity and the magnitude of the charged double ion layer accumulated at the interior surface of the capillary tube. That is, the potential at the tube exterior determines the zeta potential at a cross section of the tube.

A concern in the electrophoresis system 10 of FIG. 1 is preventing an electrical discharge from the resistive coating of the capillary tube 12 to the on-column detector 18. One alternative in addressing this concern would be to provide additional layers of insulating material over the resistive coating. However, this solution would lead to a significant loss in the sensitivity of UV detection if the additional layers were thick layers. The present invention overcomes the problem of suppressing electrical discharge by creating the external voltage gradient along the resistive coating such that the electrical potential of the portion of the coating adjacent to on-column detection is substantially equal to the electrical potential of the on-column detector 18.

Typically, the on-column detector 18 is at ground potential, so that the third and fourth high voltage power supplies 88 and 90 should be set to achieve a ground potential at the detection area of the capillary tube 12. As shown in FIG. 1, the high voltage power supply 88 connected to the inlet end 14 of the capillary tube is set at +2.7k volts. The fourth high voltage power supply 90 establishes a potential of −1.4k volts at the outlet end 16. Since the on-column detection area is conventionally closer to the outlet end 16 than to the inlet end 14, the voltage gradient along the resistive coating will be uniform only if the third high voltage power supply is set at a voltage further from ground than the fourth high voltage power supply.

Figure 3:
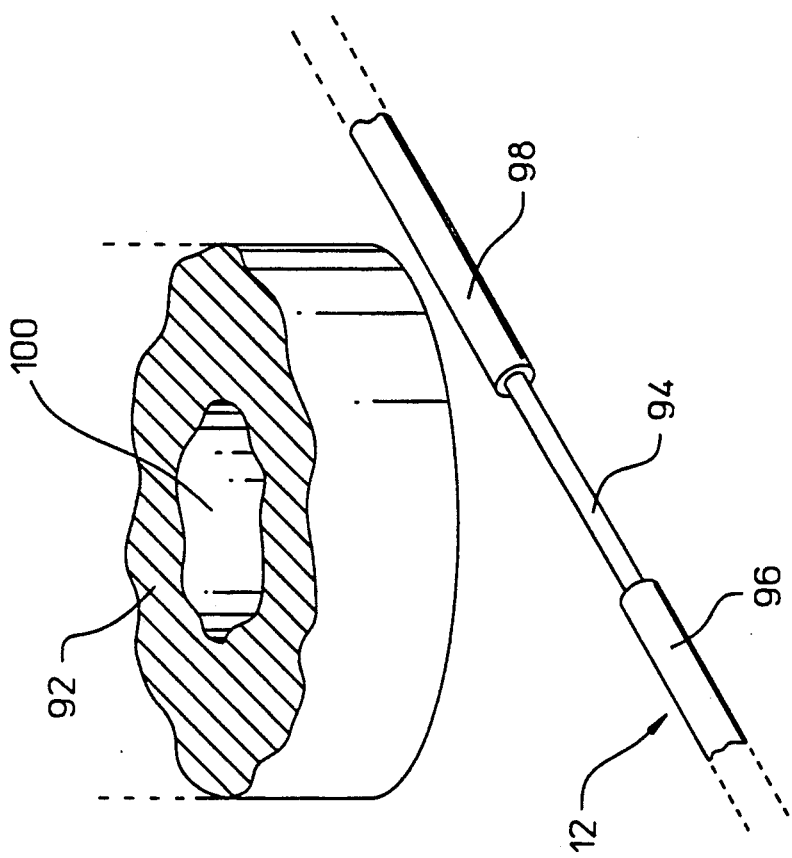
FIG. 3 is a perspective view of the capillary tube and detector of FIG. 1.

Referring now to FIG. 3, a coupling member 92 of the on-column detector is shown. The coupling member is a metallic cylindrically-shaped device having a width greater than an on-column detection window 94 of the capillary tube 12. The coupling member is structured to prevent ambient light from entering the capillary tube. Because the coupling member is metallic, it can be brought into contact with an inlet portion 96 and an outlet portion 98 of the resistive coating on the capillary tube, thereby providing an electrical bridge for linking the two portions. An aperture 100 in the coupling member defines the optical path to the detection window.

Other electrical bridges across the inlet and outlet portions 96 and 98 may be used. Electrical bridges better ensure a continuity of control of electroosmotic flow along the capillary tube 12. Alternatives for providing the electrical bridge include adhering a foil to the resistive coating at opposed sides of the detection window 94, bonding a wire across the detection window outside of the optical path of the on-column detector, and leaving a link of the resistive coating across the detection window during the process of forming the detection window.

Figure 4:
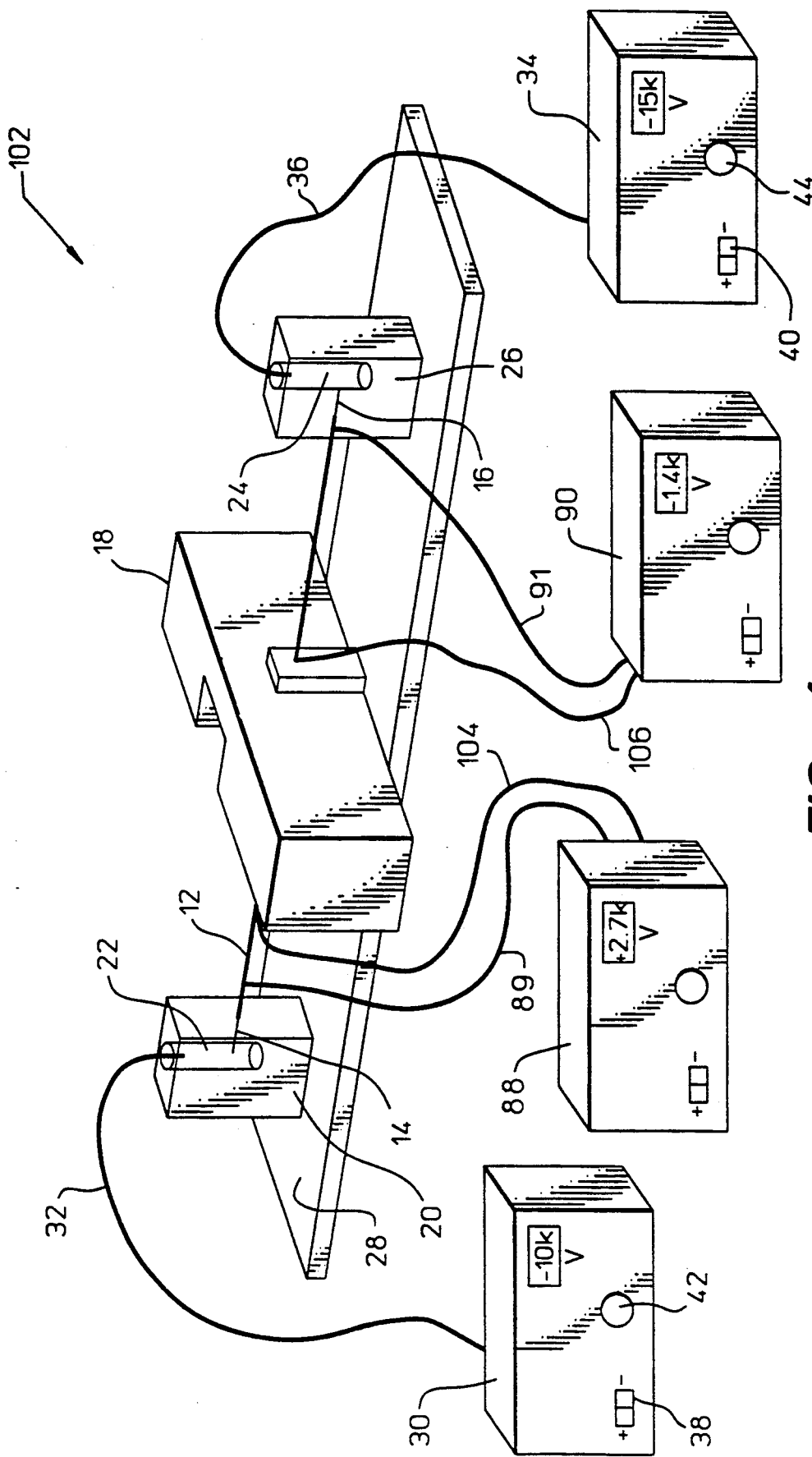
FIG. 4 is a second embodiment of an electrophoresis system, distinguished from FIG. 1 by connection of ground electrodes to a resistive coating on the capillary tube.

FIG. 4 shows another embodiment of an electrophoresis system 102 in accordance with the present invention. Because the electrophoresis system 102 includes all of the structural features of the electrophoresis system described above, the same reference numerals will be used for the common features. Where the electrophoresis system 102 differs is in the use of ground electrodes 104 and 106 from the third and fourth high voltage power supplies 88 and 90 to the resistive coating on the capillary tube 12. The grounded electrodes 104 and 106 connect to the resistive coating at regions directly adjacent to the on-column detection area of the capillary tube 12. One advantage in connecting the ground electrodes is that an electrical bridge across the detection window is effectively established without the use of foils or bond wires. Another advantage is that the attachment of the ground electrodes ensures that the point of detection is grounded and will not electrically discharge to the on-column detector 18. The second and third high voltage power supplies 88 and 90 may be set individually. Preferably, the power supplies are adjusted to ensure a uniform voltage gradient along the capillary tube, but there may be applications in which a nonuniform gradient is desired.

Referring now to FIGS. 1-3, in operation the third and fourth high voltage power supplies 88 and 90 are adjusted to establish a ground adjacent to the point of detection of the capillary tube 12. The first and second high voltage power supplies 30 and 34 are then set to achieve the desired migration of sample constituents within a sample. For a given voltage gradient along the exterior of the capillary tube, as determined by the third and fourth supplies 88 and 90, migration can be varied by corresponding adjustments to the first and second supplies 30 and 34. This is because the zeta potential at the interior of the capillary tube is a vectorial coupling of potentials determined by the four high voltage power supplies. The migration is detected by use of the UV detector 18 along an intermediate portion of the capillary tube.

While the present invention has been illustrated as using separate high voltage power supplies for creating the voltage gradient along the exterior and the interior of the capillary tube, this is not critical. Other known means for establishing desired voltages at appropriate locations along the interior and along the exterior of the capillary tube may be employed. Optimally, the potential difference of the resistive coating at the point of detection is equal to the electrical potential of the on-column detector housing, e.g., ground potential. However, what is critical is that the potential on the resistive coating and the potential of the detector housing are sufficiently close that arcing will not occur from the capillary tube to the detector housing.

While perhaps the present invention adapts most easily to use in capillary zone electrophoresis, the invention may be used with other electrophoretic separation techniques in which a capillary tube is employed. For example, the invention may be used with capillary isoelectric focusing which separates sample constituents by isoelectric point in a pH gradient formed over the length of the capillary. After the separation has been completed, electroosmotic flow may be employed in progressing the separated constituents past an on-column detector. Moreover, while the capillary column has been illustrated as a single capillary tube, the separation capillary may include more than one tube and/or more than one inlet, as in the above-cited U.S. Pat. No. 4,936,974 to Rose et al.

What is claimed is:

1. An electrophoresis system for separating sample constituents by use of electroosmotic flow and electrophoretic migration comprising,
   a capillary column having an axial bore from a first end to a second end and having an on-column detection area between said first and second ends,
   an external control means for affecting a radially directed electric field along said capillary column, thereby affecting electroosmotic flow through said axial bore, said external control means including a resistive coating on said capillary column,
   detector means aligned with said on-column detection area for sensing migration of sample constituents through said axial bore,
   first high voltage means for creating a first longitudinal voltage gradient along said axial bore of said capillary column, and
   second high voltage means in electrical communication with said resistive coating for creating a second longitudinal voltage gradient along said resistive coating, wherein electrical potential of said resistive coating varies with distance from said on-column detection area, the electrical potential of said resistive coating at a coating region adjacent to said on-column detection area being selected to inhibit electrical discharge between said resistive coating and said detector means.

2. The system of claim 1 wherein said second high voltage means provides a ground potential at said coating region of said resistive coating, said second longitudinal voltage gradient including an advancing electrical potential from said coating region toward said first end and a decreasing electrical potential from said coating region toward said second end.

3. The system of claim 2 wherein said detector means has an electrically grounded exterior.

4. The system of claim 1 wherein said second high voltage means includes first and second power supplies, said first power supply coupled to said resistive coating to provide a positive high voltage proximate to said first end, said second power supply coupled to said resistive coating to provide a negative high voltage proximate to said second end, thereby creating said second longitudinal voltage gradient.

5. The system of claim 1 wherein said detector means has an exterior fixed at an electrical potential generally equal to the electrical potential of said resistive coating at said coating region.

6. The system of claim 1 wherein said capillary column is an optically transparent capillary tube and wherein said resistive coating is an opaque coating having a split at said on-column detection area to allow on-column optical detection.

7. The system of claim 1 wherein said detector means is an ultraviolet detector.

8. The system of claim 1 wherein said resistive coating is a dielectric material having a concentration of conductive material.

9. The system of claim 1 wherein said resistive coating and said second high voltage means provide a generally uniform second longitudinal voltage gradient along said resistive coating.

10. An electrophoresis system comprising,
a longitudinal capillary tube having an inlet end to receive a sample solution to be spatially separated and having an outlet end, said capillary tube having a center bore and having a resistive layer along the length of said capillary tube,
power means for applying a first high voltage across said capillary tube to induce electrophoretic migration of sample constituents of said sample solution along said center bore and for applying a second high voltage across said resistive layer to provide a control of electroosmotic flow of said sample solution within said center bore, and
a detector aligned with said capillary tube to detect migration of said sample constituents within said capillary tube, said detector directing light to a detection area of said capillary tube between said inlet and outlet ends,
wherein said power means is electrically connected to said resistive layer in a manner to apply said second high voltage such that the electrical potential of said resistive layer approaches ground potential with approach to said detection area.

11. The system of claim 10 wherein said resistive layer has a generally uniform resistivity and wherein said power means creates a generally uniform voltage gradient with distance from said detection area.

12. The system of claim 11 wherein said resistive layer includes an opening at said detection area, said voltage gradient including an increase in voltage from said detection area with approach to one of said inlet and outlet ends and a decrease in voltage with approach to the opposite one of said inlet and outlet ends.

13. The system of claim 10 wherein said power means includes first and second high voltage supplies having ground connections at opposite sides of said detection area.

14. The system of claim 10 wherein said resistive layer is a coating of polyimide having a concentration of a conductive material.

15. An electrophoresis system comprising,
a capillary tube having an inlet end and an outlet end, said capillary tube having a resistive layer extending along a region of the capillary tube spaced apart from said inlet and outlet ends, said resistive layer having first and second portions on opposite sides of an on-column detection area of said capillary tube,
a first high voltage means connected to said resistive layer for creating the positive-going voltage gradient along said first portion of said resistive layer with increasing distance from said detection area, and
a second high voltage means connected to said resistive layer for creating a negative-going voltage gradient along said second portion of said resistive layer with increasing distance from said detection area.

16. The system of claim 15 wherein said first and second high voltage means each grounds said resistive layer at said detection area.

17. The system of claim 15 further comprising third high voltage means for creating a voltage gradient along the axis of said capillary tube.

18. The system of claim 15 further comprising an optical detector aligned with said detection area to direct light thereto, said optical detector including a grounded exterior.

19. The system of claim 15 wherein said resistive layer is an external layer.

* * * * *